(12) United States Patent
Osone et al.

(10) Patent No.: US 6,896,405 B2
(45) Date of Patent: May 24, 2005

(54) METHOD OF MEASURING THERMAL RESISTANCE OF RESIN AND A MEASURING APPARATUS USING THE METHOD

(75) Inventors: Yasuo Osone, Chiyoda (JP); Norio Nakazato, Kashiwa (JP); Takashi Kubo, Chiyoda (JP); Masaki Asagai, Tsuchiura (JP); Hiroshi Kikuchi, Hidaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/265,129

(22) Filed: Oct. 7, 2002

(65) Prior Publication Data

US 2003/0072349 A1 Apr. 17, 2003

(30) Foreign Application Priority Data

Oct. 10, 2001 (JP) .................................. 2001-312105

(51) Int. Cl.⁷ .................. G01N 25/00; G01N 25/18
(52) U.S. Cl. ...................... 374/43; 374/44; 374/46
(58) Field of Search .......................... 374/43, 44, 46

(56) References Cited

U.S. PATENT DOCUMENTS

| | | | | |
|---|---|---|---|---|
| 3,263,485 A | * | 8/1966 | Mahmoodi | 374/43 |
| 3,733,887 A | * | 5/1973 | Stanley et al. | 374/44 |
| 4,840,495 A | * | 6/1989 | Bonnefoy | 374/43 |
| 5,005,985 A | * | 4/1991 | Piórkowska-Galeska et al. | 374/44 |
| 5,258,929 A | * | 11/1993 | Tsuchida | 374/44 |
| 5,667,301 A | * | 9/1997 | Jurkowski et al. | 374/43 |
| 5,940,784 A | * | 8/1999 | El-Husayni | 374/43 |
| 6,142,662 A | * | 11/2000 | Narh et al. | 374/44 |
| 6,331,075 B1 | * | 12/2001 | Amer et al. | 374/44 |

FOREIGN PATENT DOCUMENTS

| | | | | |
|---|---|---|---|---|
| FR | 2643717 A1 | * | 8/1990 | 374/44 |
| JP | 01193635 A | * | 8/1989 | 374/44 |

* cited by examiner

*Primary Examiner*—Diego Gutierrez
*Assistant Examiner*—Mirellys Jagan
(74) *Attorney, Agent, or Firm*—Antonelli, Terry, Stout & Kraus, LLP

(57) ABSTRACT

A method of measuring a thermal resistance of laminated resin sandwiched by a first member and a second member according to the present invention includes measuring, as thermal resistance of resin, a sum of thermal resistance of an interface between the resin and the first member, thermal restistance of an interface between the resin and the second member, and thermal resistance caused by conduction of heat through the resin.

12 Claims, 13 Drawing Sheets

METHOD OF MEASURING THERMAL RESISTANCE OF RESIN AND A MEASURING APPARATUS USING THE METHOD

BACKGROUND OF THE INVENTION

The present invention relates to a method of measuring a thermal resistance of resin materials.

Industrial products using grease and resin at an interface between structural members are used over a wide range of industrial fields, for example, in the case in which a semiconductor device and a radiating plate are joined through a thermal-conductive resin, the case in which resin is molded or applied between members and then baked, the case in which gel resin is used in a state sandwiched between members, and the case in which a semiconductor device and a radiating plate are joined with an electrically conductive adhesive.

In such a product field in which heat flows through the resin, a value obtained by dividing, with an amount of passing heat, a temperature difference produced when the heat passes through the resin, that is, thermal resistance is extremely important for designing the products.

The thermal resistance of the resin comprises as its components the thermal resistance caused by conduction of heat passing through the resin itself and an interface thermal-resistance produced at interfaces between the resin and the members sandwiching the resin therebetween from both sides.

The thermal resistance caused by conduction of heat passing through the resin itself can be determined by the following equation if the flow of heat is one-dimensional.

$$R\mathrm{cond} = L/(\lambda \times A) \quad (1)$$

where Rcond is the thermal resistance caused by conduction of heat, L is a length along which the heat passes, A is a cross-sectional area in which the heat passes, and $\lambda$ is a thermal conductivity of the resin.

That is, if heat flows one-dimensionally, the thermal resistance Rcond caused by the conduction of heat through resin is proportional to the inverse of the thermal conductivity $\lambda$ of the resin.

As a technique for individually determining the thermal conductivity $\lambda$ of resin, for example, the simplest method is one usually called a stationary method, in which a test specimen having a constant sectional area A and a sufficiently long length L is made, a constant amount of heat Q is caused to flow through the test specimen, and temperature distribution of the test specimen in the direction of flowing heat is measured at a constant spacing, as shown in FIG. 2. This method itself is based on a very basic matter of heat, and a known method.

Assuming that there is a material having a thermal conductivity $\lambda$ and a sectional area A, which each are constant, and that a constant amount of heat Q one-dimensionally passes through the material, and further assuming that the spacing between positions at which temperature is measured is $\Delta L$ and a temperature difference measured is $\Delta T$, the following equation is established.

$$Q = \lambda \times A \times \Delta T / \Delta L \quad (2)$$

From the equation (2), the thermal conductivity $\lambda$ can be determined by the following equation.

$$\lambda = Q \times \Delta L / (A \times \Delta T) \quad (3)$$

That is, if an amount of passing heat Q, a sectional area A in which heat passes, and a spacing $\Delta L$ between positions at which temperature is measured are known, the thermal conductivity $\lambda$ can be experimentally determined by measuring the temperature difference $\Delta T$.

It is also possible to measure the thermal resistance Rint of an interface by using the above described stationary method.

As shown in FIG. 3, two kinds of members each having known thermal conductivities are prepared, and a constant load is applied thereon, and heat is caused to flow through them. At that time, a temperature difference $\Delta T$ in the proximity of the interface between the members is determined from changes in the temperature in each of the members, and the resultant temperature difference divided with the amount of passing heat Q corresponds to the thermal resistance Rint of the interface. Further, with respect to FIG. 2 and FIG. 3, temperature is measured at two positions in each one member. However, in order to improve reliability of the measurement, there are some methods such as making the distance $\Delta L$ between the measurement points long, and increasing the number of the temperature measurement points.

In the case of a material having a small distance L passed through by heat, that is, in the case of a thin material, as a method of measuring thermal conductivity in the direction in which heat passes through the material, that is, in the direction of the thickness of the material, an alternating-current heating method and a method using laser are used, for example. Both methods are ones to determine the thermal conductivity by measuring the thermal diffusivity of the thin material and using a thermal capacity and density measured by using other methods.

As a document disclosing the method of measuring thermal diffusivity using the alternating-current heating method, JP-A-10-221279 is indicated, for example. Further, as a document disclosing the method of using laser, JP-A-2001-83113 is indicated.

On the other hand, as documents disclosing a method of measuring the thermal conductivity of resin in a state where a load is being applied to the resin, JP-A-8-136483, JP-A-2001-21512 and the like are cited.

The above described stationary method is characterized in that as $\Delta L$ is made larger, the reliability of measurement increases. Therefore, in case of measuring the thermal conductivity of materials of which distance L passed through by heat is very small relative to the sectional area A in which heat passes, that is, thin materials such as grease used for joining a heat generating member and a heat-diffusing member and a molding resin used in a semiconductor device, it is impossible to ensure a sufficient length of $\Delta L$. For this reason, the stationary method has a problem that it is difficult to be applied to thin materials except for the case in which the thermal conductivity does not change even if the spacing $\Delta L$ between the temperature measurement positions is sufficiently increased by varying the thickness of a sample, that is, except for the case in which the thermal conductivity does not depend on the thickness of the sample. The thermal conductivity of resin is often dependent on the process of solidifying the resin and its thickness. In fact, it is needed to measure the thermal conductivity of the resin in its thin state.

Although the methods of measuring thermal diffusivity disclosed in the above described JP-A-10-221279 and JP-A-2001-83113 are characterized in that they can measure the thermal diffusivity of very thin materials, the methods are ones for measuring a temperature response when a nonstationary or transient signal of heat is provided for the materials, and require the additional measurement of specific heat and density.

In the method of measuring the thermal conductivity of resin disclosed in the above described JP-A-8-136483, there is a problem that shape of a test specimen, resin, is limited in dependent of the apparatus. That is, because a probe as a heat source is inserted in the resin, measurement is made on information including the thermal resistance of the interface between the probe and the resin. When this method is used in such a structure that the resin is sandwiched between other members from both sides in the direction of its thickness, it cannot measure the thermal resistance of the resin including the thermal resistance of its interface, except that the thermal resistance of the interface between the member and the resin is always equal to that of the interface between the probe and the resin.

Also in the method disclosed in the above described JP-A-2001-21512, it is difficult to measure the thermal resistance of resin including the thermal resistance of the interfaces between the resin and members sandwiching the resin therebetween.

On the other hand, in products using resin, there is a problem that the thermal resistance of the resin is strongly affected by manufacturing processes, information of material properties and surfaces of the members sandwiching the resin therebetween, and environments in which the resin is actually used.

For example, considering the case in which resin sandwiched between two sheets of members is baked and solidified, in general, the resin solidifies while various kinds of gas are being generated from the parent materials of the resin in the process of baking. What gas is generated depends on the material properties of the parent material of the resin and the baking process. Therefore, in order to measure thermal conductivity, when the parent material of the resin is baked with nothing present around it and a sample to be measured for thermal conductivity is cut out from the baked resin, gas is purged from the sample in each direction thereof, as shown in FIG. 4.

In contrast to this, in actual products using resin, since the parent material of resin is baked in the form in which the resin is sandwiched between other members, the direction in which gas is purged is limited to the direction in which the members sandwiching the resin therebetween are not present, as shown in FIG. 5. For this reason, the manner in which gas is purged in this case is different from the manner when there is nothing around the resin as described above, and therefore the composition and internal structure of the resin after baked are different from those of the above described sample. Thus, even if the thermal conductivity of the sample is accurately measured, it often does not conform to the thermal conductivity of the resin actually used in products.

Further, according to the temperature when products using resin are used and the temperature when the products are not used, the products may be used in the state in which the resin itself is melt, and there are cases in which the resin is re-solidified after melting and the resin repeats melting and solidifying. Thus, it is feared that due to such melting and solidification of the resin after it is mounted in products, the thermal conductivity of the resin and the thermal resistance of the interface may vary with time. In the above described case, when the variation with time of thermal resistance is not known in advance, even if only the thermal conductivity of a sample cut out from the resin without considering its mounting condition as shown in FIG. 4 is known, it often does not conform to the thermal conductivity of the resin actually used in the products, and the thermal resistance of the interface is not grasped, either.

In such a situation, when products have a structure in which heat escapes through resin, it is impossible to accurately predict a temperature rise of the products. However, in connection with such samples and actual products, conventionally, importance has not been attached to problems that a manufacturing process has an influence on the thermal resistance of the resin and that it is necessary to determine the inclusive thermal-resistance of resin including the thermal resistance of its interface. Further, in referring to data of the material properties of resin, and in legal persons and organizations or individuals, such as companies, manufacturing, selling, or distributing resin, there have been in general not found such databases arranged.

Therefore, in a product actually using resin, at the time of selecting one resin most suitable for the product concerned from among a plurality of choices of resin, users have to produce the product or a prototype close to the product and to actually measure a temperature rise of the products in which the above described choices of resin are used. Therefore, there has been a problem that a high prototyping cost and a long period are required to reach a selected resin.

The invention has an object to provide a method of measuring the thermal resistance of resin, allowing the thermal resistance of the resin to be measured in a state closest to the state in which the resin is incorporated in an actual product.

SUMMARY OF THE INVENTION

A method of measuring thermal resistance of resin according to the invention comprises sandwiching resin between a first member and a second member, and measuring, as thermal resistance of the resin, sum of thermal resistance of an interface between the resin and the first member, thermal resistance of an interface between the resin and the second member, and thermal resistance caused by conduction of heat through the resin.

A method of measuring thermal resistance of resin according to the invention comprises sandwiching resin between a first member and a second member, applying load from outside of a laminated structure consisting of the first member, the resin, and the second member to junction interfaces in the laminated structure through a third member and a fourth member, causing heat to flow in an order of the third member, the first member, the resin, the second member and the fourth member, or the fourth member, the second member, the resin, the first member and the third member through them, measuring sum of various thermal resistances of thermal resistance of an interface between the third member and the first member, thermal resistance caused by conduction of heat through the first member, thermal resistance of an interface between the first member and the resin, thermal resistance caused by conduction of heat through the resin, thermal resistance of an interface between the resin and the second member, thermal resistance caused by conduction of heat through the second member and thermal resistance of an interface between the second member and the fourth member, and subtracting sum of thermal resistance of the interface between the third member and the first member, thermal resistance caused by conduction of heat through the first member, thermal resistance caused by conduction of heat through the second member and thermal resistance of the interface between the second member and the fourth member, the thermal resistances of which have been determined in advance, from the sum of the measured-thermal resistances, whereby the sum of the thermal resistance of the interface between the first member and the resin, the thermal resistance caused by conduction of heat through the resin, and the thermal resistance of the interface between the resin and the second member is determined as the thermal resistance of the resin layer including its interface information.

The method further comprises measuring an initial value and time variation of the thermal resistance of the resin.

The method further comprises arranging as a database results obtained by measuring factors giving an influence on the thermal resistance of the resin, such as temperature, magnitude of load and humidity, and variation with time of the thermal resistance of the resin varying depending on arbitrary combinations of these factors, and applying the database to the design of thermal structure of a device on which the resin is mounted.

Also, the method further comprises measuring variation of the thermal resistance of the resin with time when factors giving influence on the thermal resistance of the resin is kept constant over a predetermined period.

Also, the method further comprises measuring variation of the thermal resistance of the resin with time when the factors giving influence on the thermal resistance of the resin are varied according to a given condition over a predetermined period.

Also, the method further comprises sandwiching the resin between members produced by specifying a material, a dimension, finishing method and finishing accuracy of surface roughness and surface waviness in a given condition, and measuring and managing, as the thermal resistance of the resin, sum of the thermal resistances of the interfaces between the members and the resin and the thermal resistance caused by conduction of heat through the resin.

Also, the method further comprises documenting the thermal resistance of the resin to store or lay to the public.

Also, the method further comprises using the thermal resistance of the resin measured using the method of measuring the thermal resistance of the resin as part of information of a product in manufacturing, selling, and distributing the resin as a product.

Also, the method further comprises using the document of the thermal resistance of resin as part of the reference for selecting the resin to be applied.

DESCRIPTION OF THE INVENTION

One embodiment of a measuring method according to the present invention will be described with reference to FIGS. 1 and 6.

Figure 1:
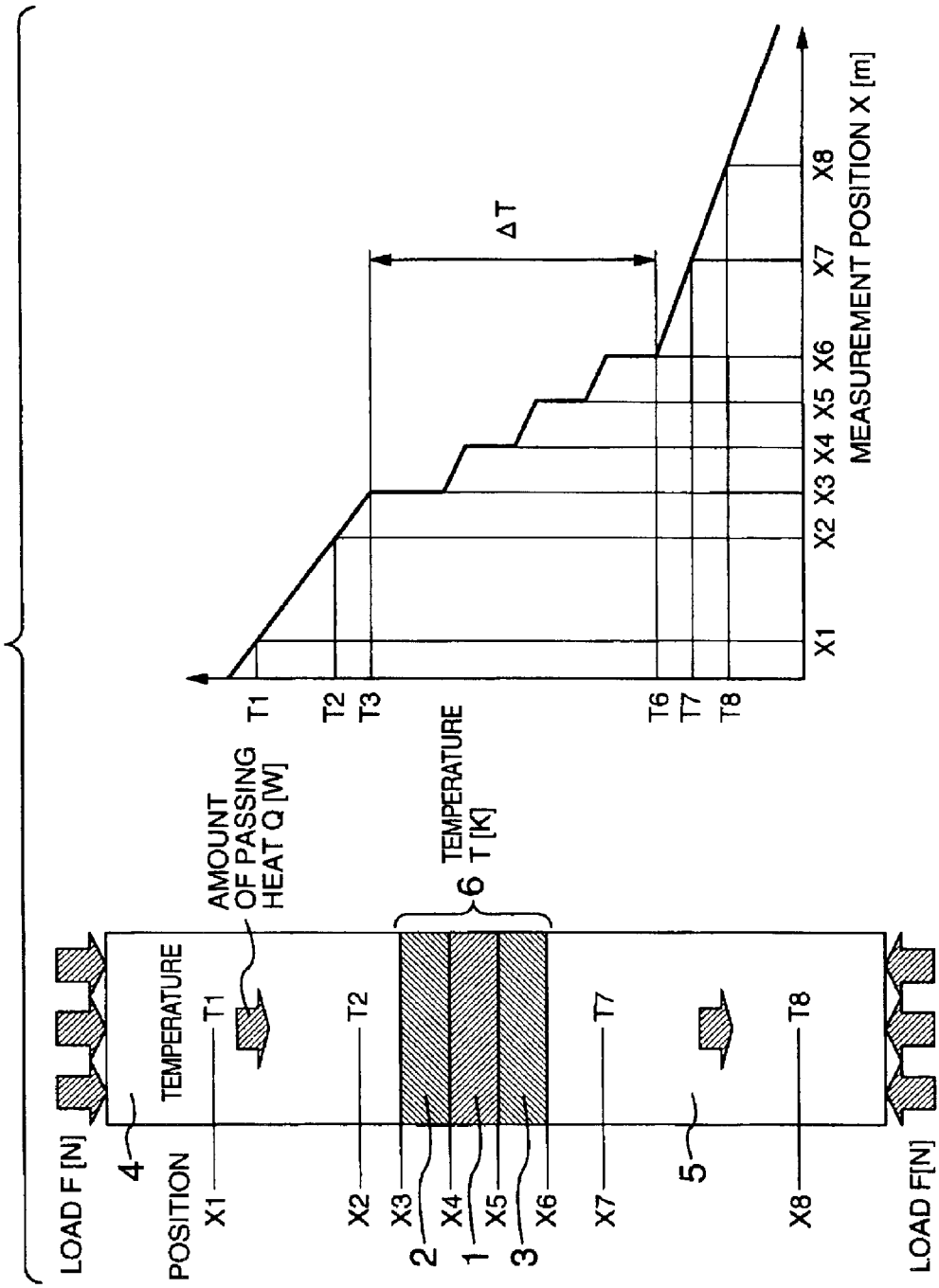
FIG. 1 is a diagram for showing a method of measuring thermal resistance of resin according to the present invention.
Figure 2:
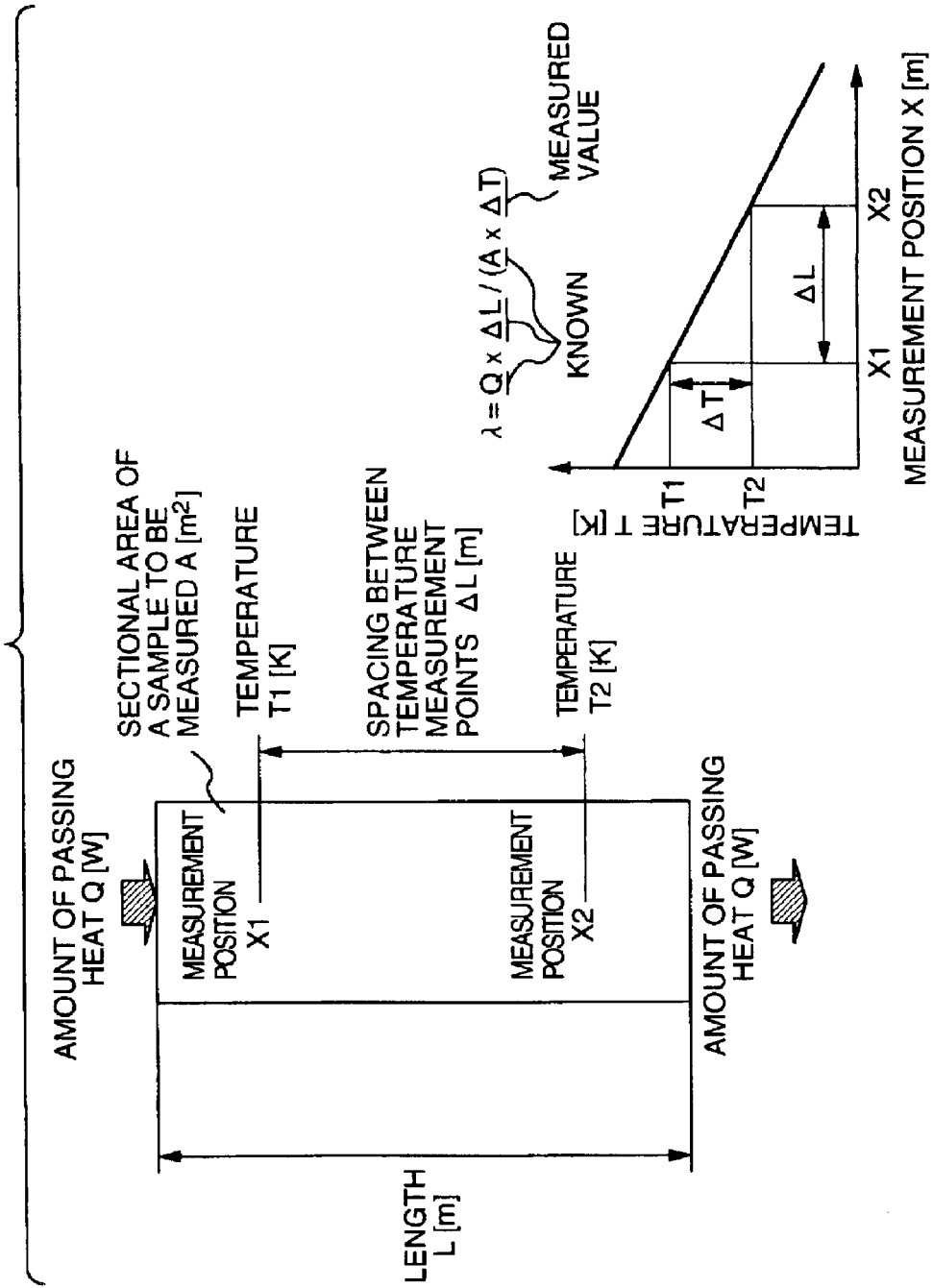
FIG. 2 is a diagram for showing a method of measuring thermal conductivity of a member according to a conventional stationary method.
Figure 3:
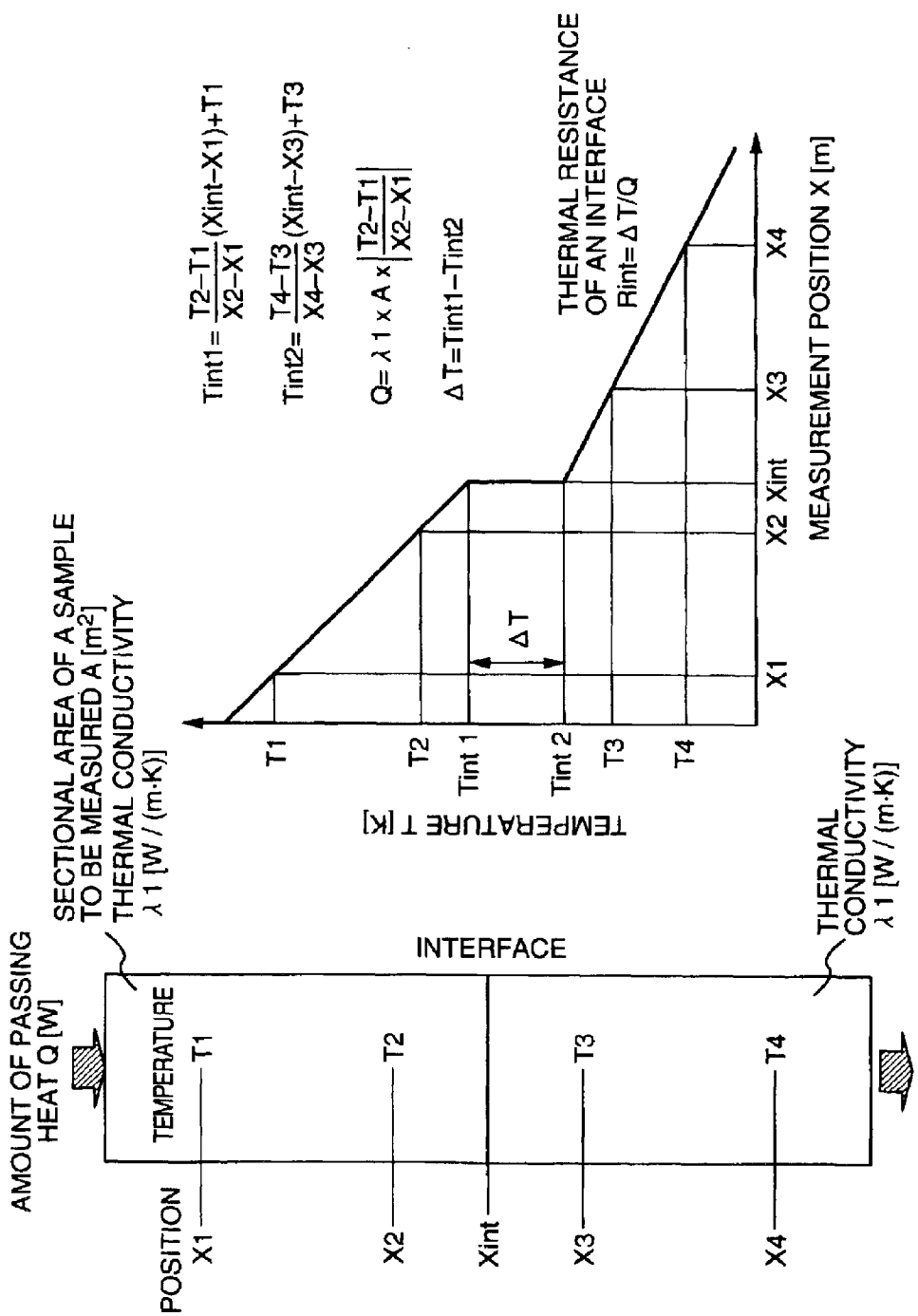
FIG. 3 is a diagram for showing a method of measuring contact thermal-resistance according to the conventional stationary method.
Figure 4:
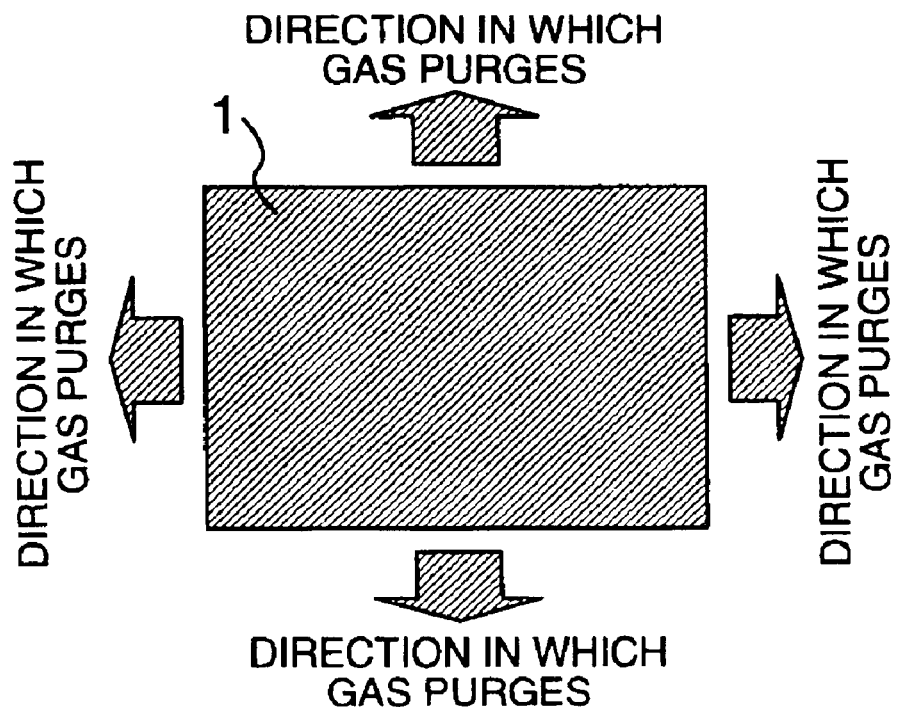
FIG. 4 is a diagram for illustrating a manner in which gas is purged from resin when nothing is present around the resin.
Figure 5:
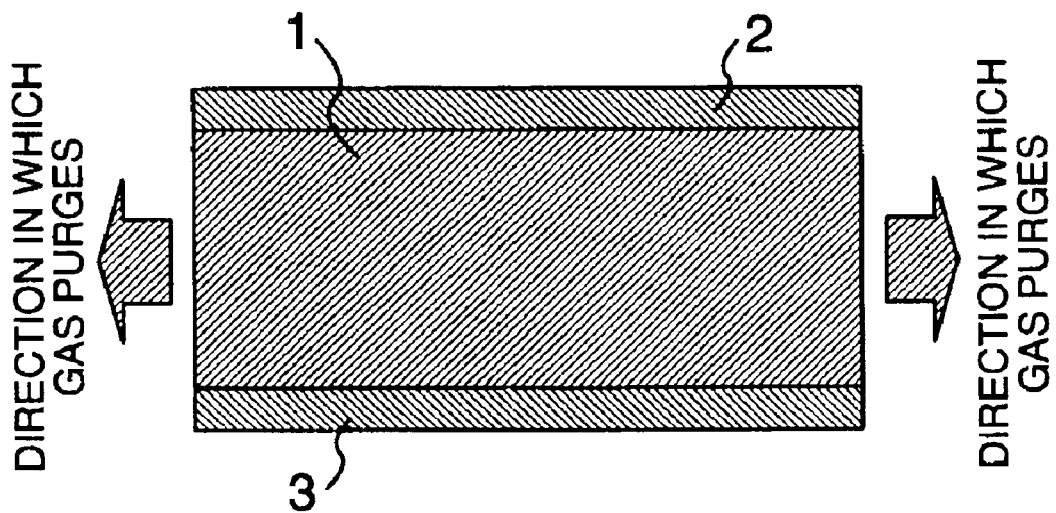
FIG. 5 is a diagram for illustrating a manner in which gas is purged from resin when resin is sandwiched between a plurality of members.

FIG. 1 is a diagram for showing a configuration for measuring thermal resistance of resin, in which the sum of the thermal resistance of an interface between the resin and a member and the thermal resistance caused by conduction of heat through the resin is measured as the thermal resistance of the whole resin by using a stationary method.

Figure 6:
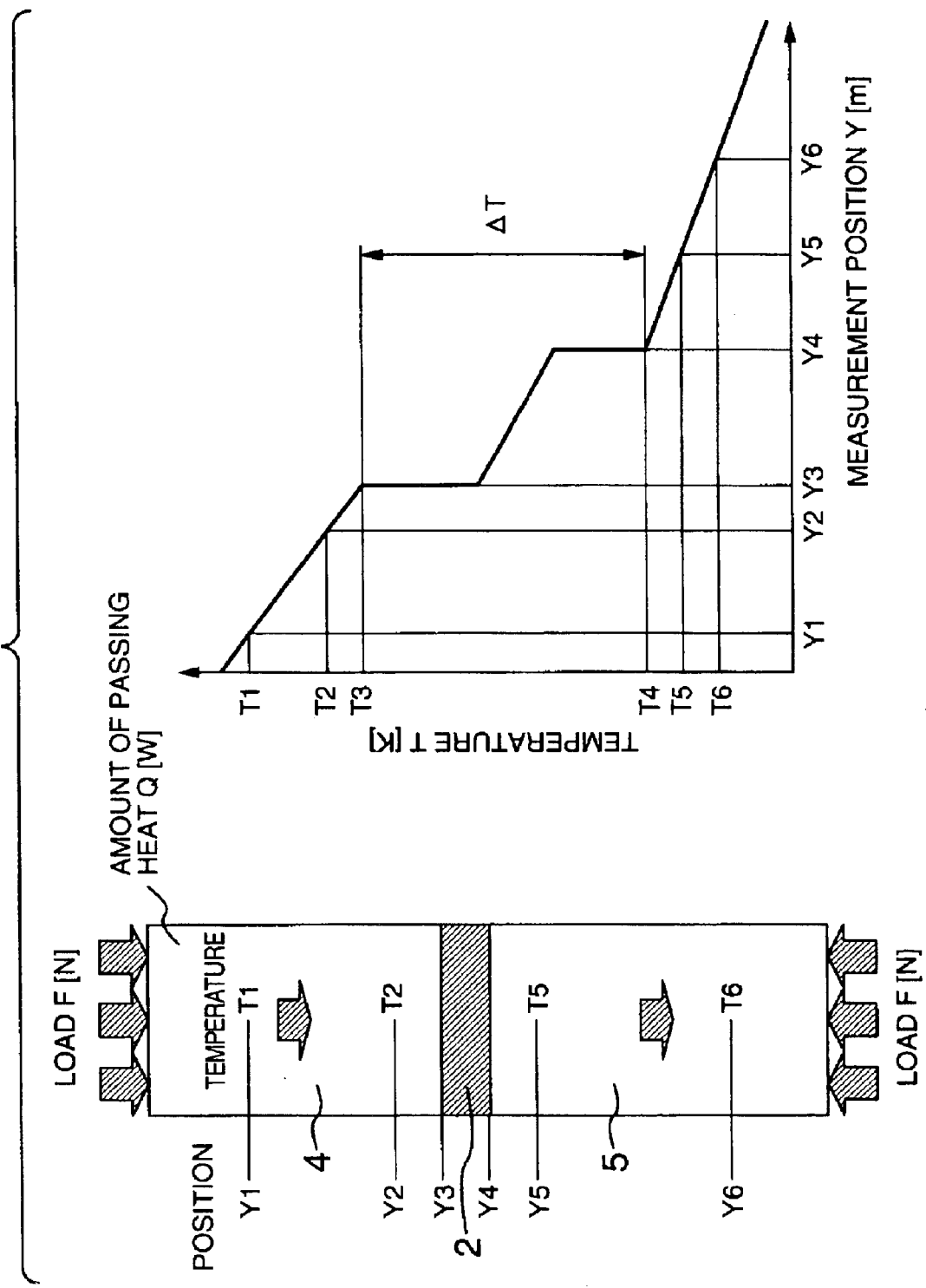
FIG. 6 is a diagram for showing a method of measuring thermal resistance of the members sandwiching resin therebetween according to the present invention.

FIG. 6 is a diagram for showing a configuration for measuring a thermal resistance of the members sandwiching the resin therebetween.

Referring to FIG. 1, resin 1 of which the thermal resistance is to be measured is set in a measuring apparatus as a test specimen of a laminated configuration in which the resin 1 is sandwiched between a first member 2 and a second member 3 in the up-and-down direction of the drawing, wherein the members 2 and 3 are manufactured by specifying the material, thickness, surface-finishing method or the like. The test specimen of a laminated configuration is, if necessary, solidified in a manufacturing process specified in advance, such as a baking process, or remains in a not solidified state.

By the way, it is desirable to make the first member 2 and the second member 3 each being almost identical in a top and a bottom surface from the viewpoint of surface waviness, surface roughness and surface-finishing method of their surfaces so that it is possible to obtain the same result whichever surface is placed to configure an interface with the resin.

The test specimen of the laminated configuration is further sandwiched between a third member 4 and a fourth member 5 in the up-and-down direction of FIG. 1, which members 4 and 5 have a function of applying a load to the test specimen or a function of keeping the thickness of the test specimen constant and a function of measuring the distributions of temperature in the members. A temperature-measuring apparatus for measuring the temperature of the members is placed at two positions in each of the third member 4 and the fourth member 5, at the positions of X1, X2, X7 and X8 in the drawing.

As the temperature-measuring apparatus, a contact type of temperature sensor such as a thermocouple is convenient, but any apparatus can be used provided that it can measure the temperature of the third member 4 and the fourth member 5 in arbitrary positions.

The number of the temperature measurement positions may be equal to or more than three for each of the third and the fourth members 4 and 5, and there is nothing wrong with continuously measuring the temperature.

Also, it is preferable that the third member 4 and the fourth member 5 coincide with each other to the extent that the materials, sectional areas, and finishing methods each are considered to be identical. Although the members 4 and 5 are preferably the same in hardness, surface waviness, surface roughness or the like, even if they are not necessarily identical, it is possible to perform measurement itself. It is not objectionable that the temperature measurement positions and the lengths of the members do not necessarily coincide with each other. If the materials of the members are different, the measurement is possible. However, it is important that the thermal conductivity λ has been measured in advance and is of a known value.

Although not shown in FIG. 1, the third member 4, fourth member 5, and laminated test specimen 6 are desirably covered all around them with a thermally insulating member in order to reduce leakage of heat caused by heat radiation from their surfaces, that is, radiation heat exchange between the ambient air and the specimen 6 or members as little as possible. Alternatively, environmental temperature may be controlled such that the average temperature of the laminated test specimen 6 may become approximately equal to the temperatures of the ambient air and structure such as an outer wall of the apparatus.

The ranges of X3 to X4, X4 to X5, X5 to X6 shown in FIG. 1 are the first member 2 for sandwiching the resin, the resin 1, the second member 3 for sandwiching the resin, respectively. In FIG. 1, a load F is applied and heat Q is caused to flow from the third member 4 toward the first member 2, the resin 1, the second member 3 and the fourth member 5.

At this time, assuming that an interface at the position X3 between the third member 4 and the first member 2 is an interface 1, an interface at the position X4 between the first member 2 and the resin 1 is an interface 2, an interface at the position X5 between the resin 1 and the second member 3 is an interface 3, and an interface at the position X6 between the second member 3 and the fourth member 5 is an interface 4, an average pressure Pav at the interfaces 1 to 4 and heat flux q through each material of a sectional area A are given the following equations.

$$Pav=F/A [Pa] \quad (4)$$

$$q=Q/A [W/m^2] \quad (5)$$

First, an amount of passing heat Q [W] can be determined based on this measurement. Assuming that the thermal conductivities of the third member 4 and the fourth member 5 are λ4 and λ5 [W/(m·K)], respectively, the following relations are obtained.

$$Q=\lambda 4 \times A \times |(T2-T1)/(X2-X1)| \quad (6)$$

$$Q=\lambda 5 \times A \times |(T8-T7)/(X8-X7)| \quad (7)$$

When the thermal insulation of the measuring apparatus is not enough, heat leaks to their surroundings while heat is flowing from the third member 4 to the fourth member 5. As a result, although there is a case that calculated amounts of heat Q passing through the third member 4 and the fourth member 5 do not coincide with each other, it is desirable to ensure a method of thermally insulating the system such that this difference may be smaller than minimum scale value from the viewpoint of measurement. For example, the methods are considered in which the measuring apparatus is placed in a constant temperature furnace to control the atmosphere temperature such that the approximate average temperature from the third member 4 to the fourth member 5 may be approximately equal to the temperature of the ambient environment, and in which the measuring apparatus is covered with materials of extremely low thermal-conductivity.

On the other hand, the temperature T3 [K] of the third member 4 on the interface 1 and the temperature T6 [K] of the fourth member 5 on the interface 4 can be determined from the amount of passing heat Q and the thermal conductivities λ4 and λ5. That is, $$T3=(T2-T1)/(X2-X1) \times (X3-X1)+T1 \quad (8)$$

$$T6=(T8-T7)/(X8-X7) \times (X6-X7)+T7 \quad (9).$$

The thermal resistance including interface information Rtot [K/W] can be determined from the amount of heat Q obtained from the equation (6) or (7) and the difference ΔT=T3−T6 between the temperature T3 of the third member 4 on the interface 1 and the temperature T6 of the fourth member 5 on the interface 4.

$$Rtot=\Delta T/Q \quad (10)$$

This Rtot includes the thermal resistance of the interfaces Rint1 to Rint4 from the interface 1 to the interface 4, and the thermal resistances Rcond1, Rcond2, and Rcond3 caused by conduction of heat through the resin 1, the first member 2, and the second member 3, respectively. That is, $$Rtot=Rint1+Rcond2+Rint2+Rcond1+Rint3+Rcond3+Rint4 \quad (11).$$

Among them, the thermal resistance of the resin to be determined is assumed to be R, and then R can be expressed the following equation.

$$R=Rint2+Rcond1+Rint3 \quad (12)$$

Thus, it is necessary that Rint1, Rcond2, Rcond3, and Rint4 have been determined in advance. How to determine these elementary thermal resistances will be described with reference to FIG. 6.

FIG. 6 is a diagram for showing a configuration for measuring the thermal resistance of the first member 2 and the second member 3 sandwiching the resin therebetween. Herein, the configuration including the first member 2 is shown, but the measurement for the second member 3 can be performed by the same method.

The third member 4 and the fourth member 5 are assumed to be produced with identical materials equal in thermal resistance and hardness, and also assumed to have equal sectional areas. Also, the surface waviness, surface roughness, and surface-finishing method of their surfaces are specified in the same condition and finished, and as a result, the surfaces of the members 4 and 5 are assumed to be the same within a range of statistical error. Further, with regard to the first member 2, as described above, the surface waviness, surface roughness, and surface-finishing method are specified in the same condition for the top and bottom surfaces and finished, and as a result, the top and bottom surfaces are assumed to be the same within a range of statistical error.

The first member 2 is sandwiched between the third member 4 and the fourth member 5, and load F is applied to them from both sides, and a constant amount of heat Q is caused to flow through them. It can be said from the above described conditions that the interface between the third member 4 and the first member 2 and the interface between the fourth member 5 and the first member 2 each are substantially identical with the interface between the third member 4 and the first member 2 in FIG. 1. For this reason, the amount of passing heat Q is calculated from the temperatures measured at temperature measurement points Y1, Y2, Y5, and Y6 by the same technique as in FIG. 1, and further the respective temperatures T3 and T4 of the third member 4 and fourth member 5 on the interfaces of positions Y3 and Y4 are determined, and then a value obtained by dividing the difference $\Delta T = T3 - T4$ by the amount of passing heat Q is the thermal resistance R2 of the member 2 including interface information. That is, $$R2 = R\text{int}1 + R\text{cond}2 + R\text{int}1 \quad (13).$$

Thus, R2 can be measured with the same apparatus as the experimental apparatus shown in FIG. 1.

By the way, because Rcond2 is uniquely defined from the thermal conductivity and sectional area of the first member 2, it should be unnecessary to measure Rcond2, but it can be also measured according to the following procedure. As understood from the equation (2), if the thermal conductivity, sectional area, and amount of passing heat each are the same for each, a measured temperature difference $\Delta T$ is proportional to the length $\Delta L$ along which heat passes. For this reason, a plurality of members different in length in the direction of passing heat, i.e. in thickness are prepared as the first member 2, and measurement is performed on them in the same manner.

For example, it is considered to measure the first members 2 of two kinds of a standard thickness $\Delta L$ and a n-times thickness n $\Delta L$. Assuming that the thermal resistance in the case of the thickness $\Delta L$ is R2 and the thermal resistance in the case of the thickness n $\Delta L$ is R2_nL, the following equations are obtained.

$$R2 = R\text{int}1 + R\text{cond}2 + R\text{int}1 \quad (14)$$

$$R2\_nL = R\text{int}1 + n\, R\text{cond}2 + R\text{int}1 \quad (15)$$

Therefore, by measuring R2 on a plurality of the first members 2 that are different only in the thickness, it is possible to determine the thermal resistance Rcond2 caused by conduction of heat passing through the first member 2, and the thermal resistance Rint1 of the interface.

$$R\text{cond}2 = (R2\_nL - R2)/(n-1) \quad (16)$$

$$R\text{int}1 = (R2 - R\text{cond}2)/2 \quad (17)$$

Further, although n represents generally a natural number, n may be a real number, provided that measurement can be accurately performed.

Also, by carrying out the method of FIG. 6 for the second member 3 and fourth member 5 in the same manner, it is possible to measure the thermal resistance Rcond3 caused by conduction of heat passing through the second member 3 and the thermal resistance Rint4 of the interface between the second member 3 and the fourth member 5.

Further, when the third member 4 and the fourth member 5 can be considered to be different members having substantially different surfaces because the members 4 and 5 are different, for example, in the materials and finishing methods thereof or different in the surface waviness, surface roughness, and surface-finishing method of their surfaces, a plurality of the third members 4 and the fourth members 5 are prepared respectively, and a measurement on the configuration consisting of the third member 4, the first member 2 and the third member 4 and a measurement on the configuration consisting of the fourth member 5, the second member 3 and the fourth member 5 are separately carried out, thereby measuring Rint1, Rint4, Rcond2, and Rcond3.

As described above, according to the technique shown in FIG. 1 and FIG. 6 and using the substantially identical measuring-apparatuses, the thermal resistances Rint1 to Rint4 of a plurality of the interfaces and the thermal resistances Rcond1 to Rcond3 caused by conduction of heat are measured, thereby allowing measurement of the thermal resistance R to be determined.

Next, a method of producing a measurement sample according to the present embodiment will be described. The embodiment is characterized in that the resin 1, the first member 2 and the second member 3 sandwiching the resin 1 therebetween are stacked in a laminated configuration in the order of the first member 2, the resin 1 and the second member 3 in the direction of passing heat.

In this case, the first member 2 and the second member 3 correspond to, for example, a lead frame and an insulating layer or a radiating plate or a heat-diffusing plate, and a semiconductor element or a heat-diffusing plate having the semiconductor element mounted thereon and a wiring board or a radiating plate in a molded semiconductor module. However, they may be applicable to any structure in which heat is transferred from a certain member to another member through resin.

The laminated sample 6 comprising the first member 2, the resin 1, and the second member 3 is produced according to a process approximately identical with the actual manufacturing process of a user using the resin 1, or a standard process defined by a supplier supplying the resin 1 based on the approximately standard process of a user using the resin 1 as a product.

In this case, such a fact itself should be included in the present invention that the thermal resistance of the resin 1 including the information of its interface is measured using the methods of FIG. 1 and FIG. 6 on the sample produced by defining a standard process, and that the measuring method is standardized, and that the thermal resistance of the resin 1 is measured on a sample produced according to a process approximately compliant with the manufacturing process of a user of the resin 1.

Also, when samples for the first member 2 and the second member 3 sandwiching the resin 1 therebetween are produced according to a process approximately compliant with the manufacturing process of a user of the resin 1, the present invention includes using a material sharing an interface with the resin 1 of actual products as the material of the first member 2 and the second member 3. Further, the present invention includes that a supplier of the resin 1 determines a standard process and defines the material, thickness, and surface-finishing method of the first member 2 and the second member 3, to measure the thermal resistance of the resin 1 including its interface.

Further, it goes without saying that the present invention includes arranging as a database the above described thermal resistance of the resin 1 including its interface, distributing the database at cost or no cost, introducing the database in a technical document for selling and distributing the resin 1, and using the database as a document for a product in which the resin 1 is used.

In the present embodiment, as parameters for producing the laminated sample 6 consisting of the first member 2, the resin 1, and the second member 3, there are the sectional area in which heat passes during the measurement of thermal resistance, and the thickness of each member in the direction of passing heat, in addition to the material, the surface waviness, the surface roughness, the finishing method of the surfaces thereof, and surface treatment such as annealing of the first member 2 and second member 3. Also, in case of baking and solidifying of the resin 1, the parameters include all the conditions for a shape, process or the like used in mounting the resin 1 on products, such as a method of controlling the temperature profile and ambient in the baking and solidifying, wherein conditions are different according to the material of the resin 1 and the method of using it.

By the way, although the thermal resistance of resin including its interface generally varies with time, conventionally, suppliers manufacturing, selling and distributing the resin have not been able to possess the data concerning this variation with time in a standardized form. The present invention also includes measuring the time variation of the thermal resistance of resin including its interface to use the results in a document of thermal resistance. At this time, for example, load, environmental temperature, and environmental humidity may be included as a control parameter. Also, when the resin is not solidified, the thickness of the resin may be included in the parameters.

The present invention includes measuring the variation with time of the thermal resistance of resin including its interface by keeping respective predetermined values of the above described control parameters constant over time, and changing the parameters with time according to a set profile, and managing the measuring method used and the measured results as physical property information of the resin.

Whatever the case may be, the invention is characterized in that the thermal resistance including the interfaces in a configuration of member, resin and member, and the thermal resistance of resin after being metamorphosed through the processes of curing and baking or including the case in which the resin is not metamorphosed are measured according to the methods shown in FIG. 1 and FIG. 6 and other methods, and that before users of resin mount the resin on their products, a third party entrusted in any form from the supplier of the resin or the supplier or the user, or a third party not belonging the above described third party has previously measured the thermal resistance of an interface of the resin concerned, in themselves.

Another embodiment according to the invention will be described with reference to FIG. 7.

Figure 7:
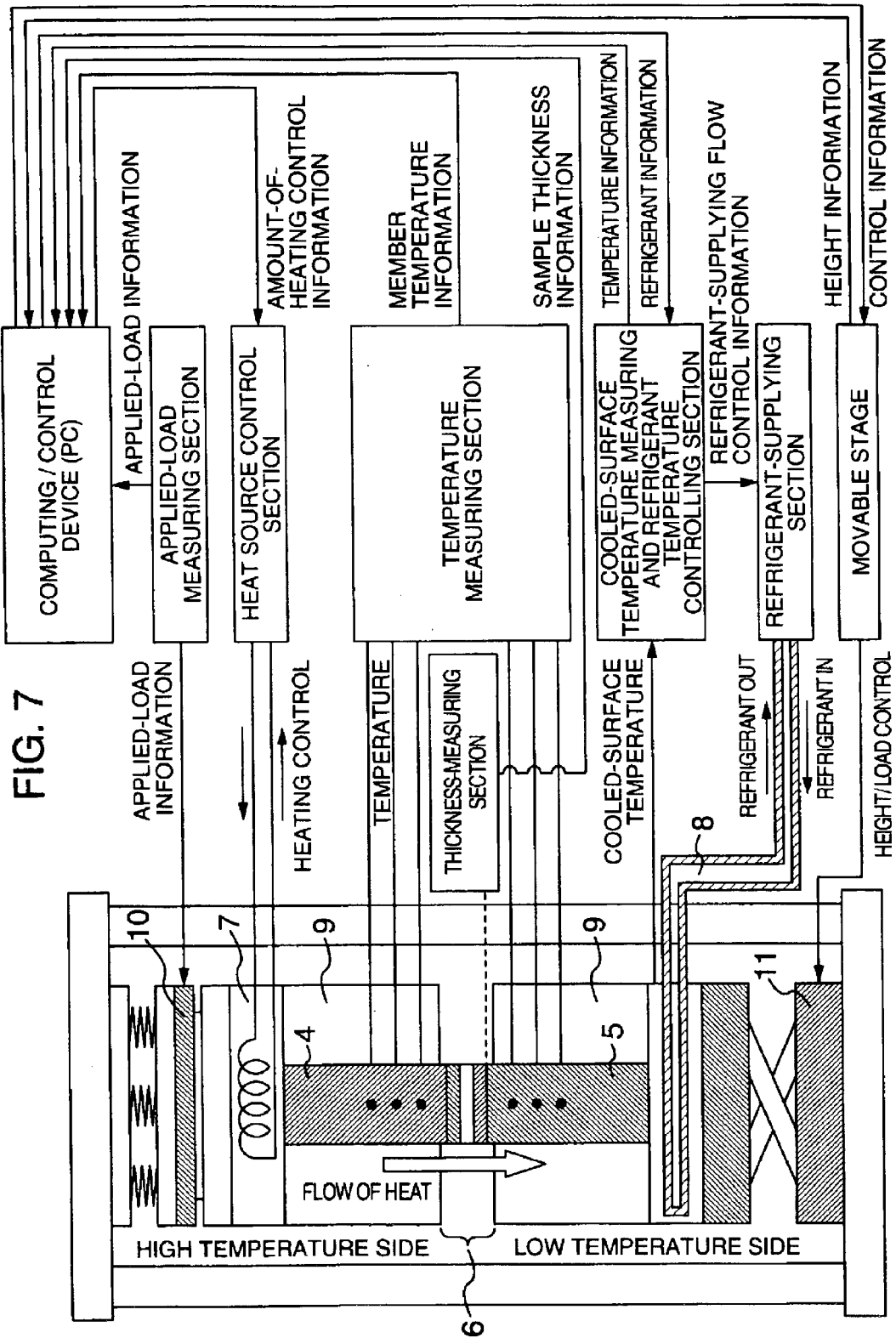
FIG. 7 is a diagram for showing a configuration of an apparatus for measuring thermal resistance of resin including information of its interface when a load applied on the resin is controlled.

FIG. 7 is a diagram for showing a configuration of a measuring apparatus when load is kept constant or when a time-based load profile of load is defined and load is changed according to it, that is, load is controlled to measure the thermal resistance of resin including its interface.

In FIG. 7, the measurement of the thermal resistance of resin including its interface by controlling load in such a manner is particularly effective when changes in the length or thickness of the resin in the direction of passing heat or in the direction parallel to the load are small relative to the changes of the load and the elapsed time. However, needless to say, it is an effective method for the resin that does not correspond to the above described conditions.

A measuring apparatus for the thermal resistance of resin according to the present embodiment comprises, as its basic configuration, the laminated sample 6 consisting of the resin 1 and the first member 2 and the second member 3 sandwiching the resin 1 therebetween, and the third member 4 and the fourth member 5 for applying heat and load to the laminated sample 6.

FIG. 7 shows a configuration in which heat flows from the upper side of the drawing toward the lower side thereof. However, with regard to the direction in which heat is caused to flow, the same effect can be obtained even if the direction is downward vertically or upward vertically or in the other direction, provided that the structure allows heat to flow one-dimensionally in the order of the third member 4, first member 2, resin 1, second member 3 and fourth member 5 or in the reverse order to it.

Among them, FIG. 7 shows the case in which heat flows in the vertically downward direction, downward from the top of the drawing. In this case, a heat source 7, such as a heater, is placed in the proximity of the third member 4 to provide a heat signal, and a cooling device 8, such as a water cooling module, is placed in the proximity of the fourth member 5, thereby allowing the temperature of the laminated sample 6 to be controlled to an arbitrary value. The third member 4 and the fourth member 5 are covered with a heat insulating material 9 all around them, and thereby, the heat flowing from the third member 4 to the fourth member 5 through the laminated sample 6 can be prevented from leaking to the outside of the apparatus via radiation and convection heat-transfer with ambient environment such as the air.

When atmosphere control is possible to allow the temperature of ambient environment to be kept approximately equal to the typical temperature of the laminated sample 6, even if a heat insulation effect by the heat-insulating material 9 is not enough, the leakage of heat can be suppressed to a small extent.

An average value of pressures at the interfaces between the laminated sample 6 and the third member 4, the fourth member 5 is equal to an applied load divided by a sectional area. For this reason, the magnitude of the applied load is measured by a load-measuring device 10 such as a load cell, and the height of a stage 11 is controlled based on the results, thereby allowing the magnitude of the load to be kept constant, or the magnitude of the load to be kept at a set value according to a time-based profile of load.

In the present embodiment, FIG. 7 shows a measuring system for a single sample, but a unit for measuring a plurality of samples may be provided in the identical apparatus. Also, although FIG. 7 shows a position relation such that the laminated sample 6 is placed between the stage 11 for controlling load and the load-measuring device 10, the structure is not limited to the structure in which the laminated sample 6 is placed between the stage 11 and the load-measuring device 10.

Another embodiment according to the invention will be described with reference to FIG. 8 and FIG. 9.

Figure 8:
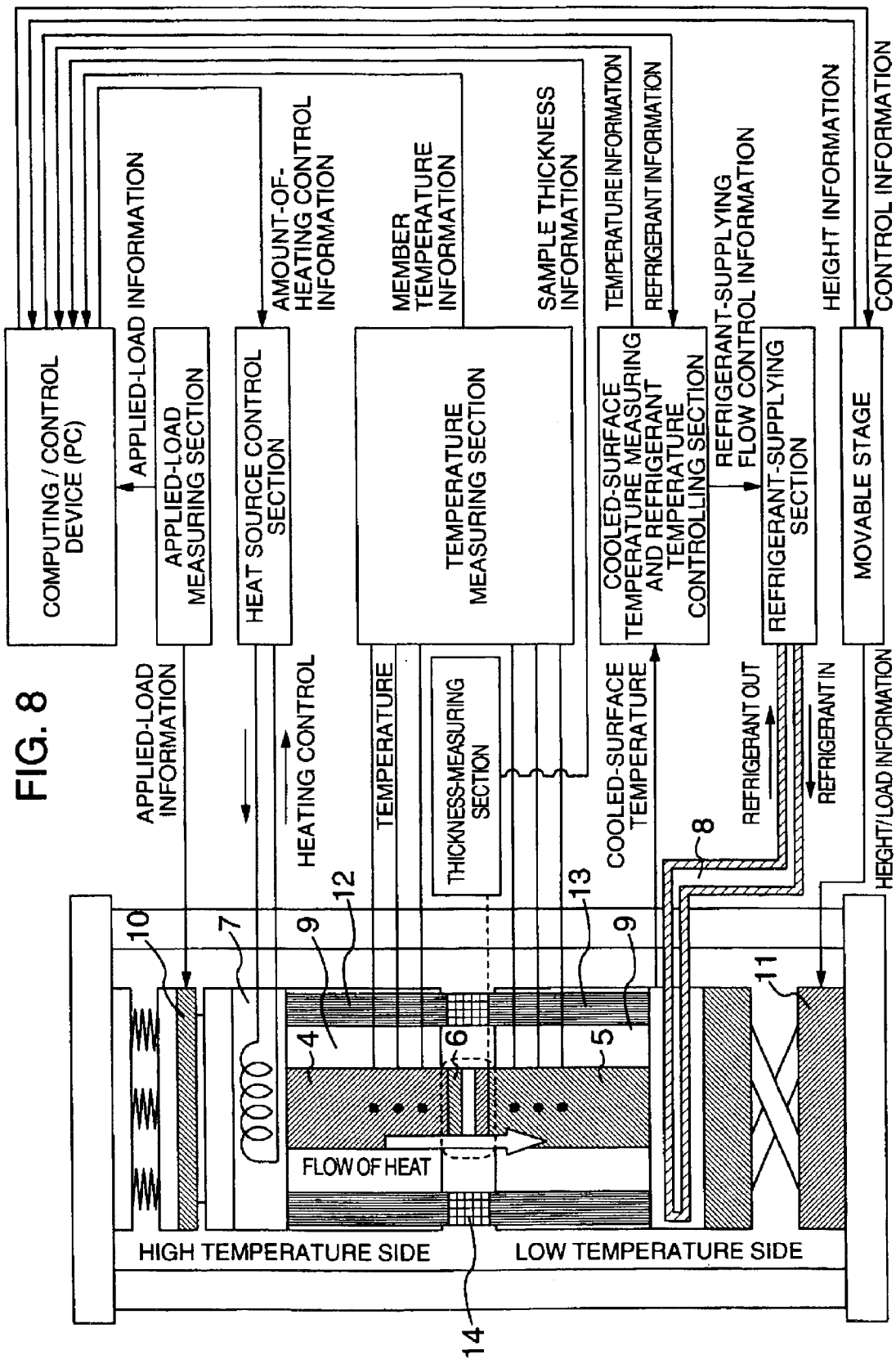
FIG. 8 is a diagram for showing a configuration of an apparatus for measuring thermal resistance of resin including information of its interface when a thickness of the resin is controlled.

FIG. 8 is a diagram for showing a configuration of an apparatus for measuring the thermal resistance of resin including its interface by controlling the thickness of the laminated sample 6 to a constant condition.

The measurement of the thermal resistance of resin including its interface by controlling the thickness in this manner is effective for the case in which when load is applied on the resin for a long time, the resin becomes deformed or flows out or protrudes from between the first member 2 and the second member 3 because the resin is of a flexible structure and a grease-like or gel-like material or because of other reasons. That is, the present measuring method is effective for the case in which changes in the thickness of the resin is large relative to changes in the load or the elapsed time, but needless to say, it is also effective when the resin does not correspond to the above.

As shown in FIG. 8, there are placed a fifth member 12 and a sixth member 13, and a spacer 14 for defining the thickness, in addition to the laminated sample 6 and, the third member 4 and the fourth member 5 sandwiching the sample 6 therebetween. For the lengths of the third member 4 and the fifth member 12, and the lengths of the fourth member 5 and the sixth member 13, it is desirable that the respective lengths becomes equal during any test.

For example, in the case shown in FIG. 8, a group of the third member 4, the laminated sample 6 and the fourth member 5 and a group of the fifth member 12, the spacer 14 and the sixth member 13 share the identical heat source 7 and the identical cooling device 8. However, it is effective that each of the groups separately has the heat source 7 and the cooling device 8, and that the third member 4 and the fifth member 12, the fourth member 5 and the sixth member 13 are of the identical materials, identical dimensions and identical surface-finishing, and thus an amount of heat passing through them and their temperature distributions are controlled to be equal. As a result of such procedures, the bottom surfaces of the third member 4 and the fifth member 12 are placed in the same plane and the top surfaces of the fourth member 5 and the sixth member 13 are placed in the same plane. When the up-and-down direction in the drawing coincides with vertical up-and-down direction as is, it can be said that each of the groups are placed in separate identical horizontal plane. The thickness of the spacer 14 is selected to be equal to a thickness that is desired to be kept constant as the thickness of the laminated sample 6.

Particularly, in the cases in which the temperature of atmosphere is kept constant at a condition of high temperature or it is periodically changed, the side including the laminated sample 6 and the side including the spacer 14 are made as equal as possible in the coefficient of thermal expansion, amount of passing heat and temperature distribution of each member, thereby allowing the thickness of the laminated sample 6 to be controlled to a constant.

Also, it is desirable that the spacer 14 is made of a material that is as small as possible in coefficient of thermal expansion. When such a material is used, a case may be resulted in which sum of the thermal resistance of the whole laminated sample 6 including the thermal resistances caused by conduction of heat through the resin 1 and each member 2, 3 and the thermal resistances of the interface between the resin 1 and the member 2 and the interface between the resin 1 and the member 3, and the thermal resistances of the interface between the laminated sample 6 and the member 4 and the interface between the laminated sample 6 and the member 5 does not necessarily coincide with sum of the thermal resistance caused by conduction of heat through the spacer 14 and the thermal resistances of the interface between the spacer 14 and the members 12 and the interface between the spacer 14 and the member 13, an therefore, a difference between the temperature distributions may occur. In such a case, by changing the sectional area of the spacer 14, the shape of the spacer 14 can be tuned such that two kinds of the paths of passing heat may be equal in thermal resistance.

In the present embodiment, the thickness of the laminated sample 6 can be kept constant by using the spacer 14. Therefore, by using this method, it is possible to prevent the resin 1 from greatly deforming apart from a product shape of the resin 1, or from protruding or flowing out from between the first member 2 and the third member 4 due to the fact that the resin 1 is of a flexible structure or a grease-like or a gel-like material when a load is applied to keep the thickness at constant. Thereby, it is possible to measure the thermal resistance of the resin 1 including the information of its interface.

FIG. 8 shows the configuration in which the spacer 14 is provided at two positions in the measuring apparatus by using the fifth member 12 and sixth member 13. However, the spacer 14 can be provided at one position, provided that it is possible to keep a constant thickness of the laminated sample 6 in which the resin 1 is sandwiched. Also, in the case of a so-called multi-stack type configuration allowing simultaneous measurement of a plurality of the laminated samples 6, the spacer 14 may be sandwiched between the first member 2 and the second member 3 in a test unit in which the laminated member 6 is not provided.

Figure 9:
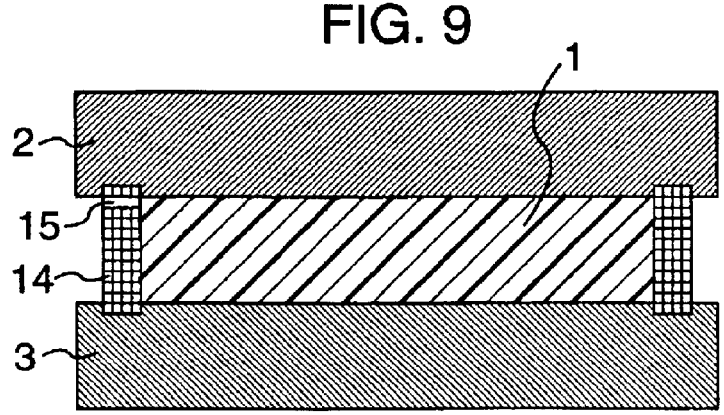
FIG. 9 is a diagram for showing an example of a configuration of a spacer when a thickness of the spacer is controlled.

FIG. 9 is a diagram for showing a configuration of the laminated sample 6 including the spacer 14 when the resin 1 may flow out from between the first member 2 and the second member 3 for a long time because the resin 1 is a grease-like or gel-like member.

As shown in FIG. 9, grooves are formed in the vicinity of the outer peripheries of facing surfaces of the first member 2 and the second member 3, and frame-like spacers 14 are fit in the grooves. In producing the laminated sample 6, the spacers 14 are fit in the grooves of the first member 2 or the second member 3 to be placed in the lower side of the sample 6 in the vertical direction, the resin 1 is put into a resultant container-like space, and then the other remaining member is fit from above, thus producing the laminated sample 6. In this case, it is preferable that the thermal conductivity of the spacer 14 has a value as small as possible, that is, the spacer 14 is desirably of a material able to be used as a heat insulating material. Also, needless to say, the spacers 14 is desirably of a material of which coefficient of thermal expansion is as small as possible.

Further, when a void remains between the resin 1 and the first member 2 and between the resin 1 and the second member 3, the structure of the interfaces between the resin 1 and each of the members 2 and 3 can be different from the structure of the interfaces between the resin 1 and each of the members 2 and 3 when the resin 1 is mounted on products. For this reason, for example, a drain 15 as shown in FIG. 9 is provided in the spacer 14 to leak the resin 1 filled too much and air, and in the final process step for producing the laminated sample 6, the drain 15 is filled in with the same material as the spacer 14 or another filling material of low thermal conductivity, thereby preventing the generation of voids, the variation of thickness, and the flowing out of the resin 1.

Also in the embodiment shown in FIG. 9, by having measured in advance the thermal resistance of a case including no resin 1, only the first member 2, the spacer 14 and the second member 3, it is possible to oppositely calculate the thermal resistance of the resin 1, which is the sum of the thermal resistance $R_{int2}$ of the interface between the first member 2 and the resin 1, the thermal resistance $R_{cond2}$ caused by conduction of heat through the resin 1, and the thermal resistance $R_{int3}$ of the interface between the resin 1 and the second member 3, which form a heat flow in parallel with the spacer 14.

Other embodiment of the invention will be described with reference to FIG. 10. The present embodiment is characterized in that, in addition to the heat source 7 and the cooling device 8 for applying heat to the laminated sample 6, an auxiliary heat source 16 and an auxiliary cooling device 17 for controlling the respective temperatures of the third and fourth members 4 and 5 are provided in peripheries of the third member 4 and the fourth member 5 in an unit for measuring the thermal resistance including the information of individual interfaces of the laminated sample 6. The auxiliary heat source 16 may be, for example, a sheet heater and an electrical resistor, and the auxiliary cooling device may be, for example, piping through which refrigerant circulates. Both of them are used to control the temperatures of the third member 4 and the fourth member 5.

In case of measuring the thermal resistance of the resin 1 including the information of its interface, some cases requires that, for example, the whole measuring apparatus is set in a constant temperature furnace and the atmosphere temperature thereof is periodically changed for measuring the variation with time of thermal resistance. In such cases, because of the effect of the heat capacity of the whole measurement system including the laminated sample 6, there is a problem that the temperature variation of the measurement system cannot follow the control of the atmosphere temperature, except for the case in which the modulation period of the atmosphere temperature is long enough.

As a result of this, when the atmosphere temperature is modulated, the respective constituent members play roles of thermal capacitors, resulting in the case in which amounts of heat passing through the third member 4, the laminated sample 6, and the fourth member 5 are respectively different. Under such conditions, it is impossible to measure the thermal resistance of the laminated sample 6 and the thermal resistance of the resin 1 including the information of its interfaces by means of the methods shown in FIG. 1 and FIG. 6.

In the present embodiment, by controlling the auxiliary heat source 16 and the auxiliary cooling device 17 in accordance with the modulation of atmosphere temperature, it is possible at all time to keep constant the amount of passing heat for measuring the thermal resistance, which heat passes through the third member 4, laminated sample 6, and the fourth member 5. Thereby, it is possible to measure the variation with time of the thermal resistance of the resin 1 including its interfaces when the atmosphere temperature is periodically changed.

Figure 10:
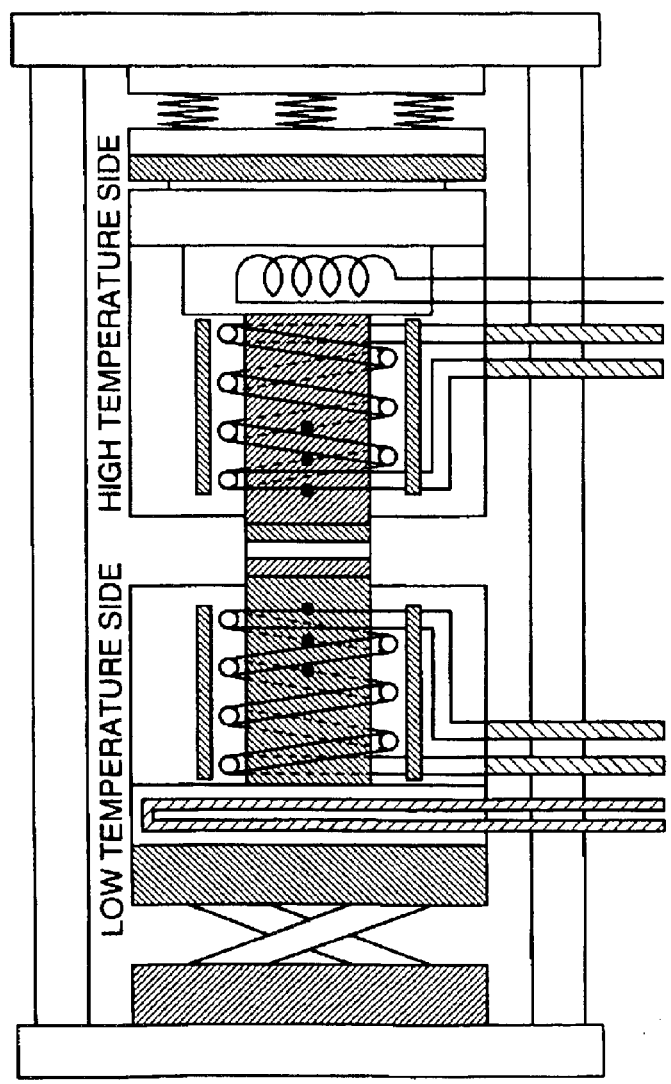
FIG. 10 is a diagram for showing a configuration of a measuring apparatus when an auxiliary temperature-controlling function is incorporated.

By the way, although an atmosphere environment-controlling apparatus such as a constant temperature furnace is not shown in FIG. 10, it goes without saying that such an atmosphere environment-controlling apparatus is effective temperature-controlling means.

Methods of disclosing the data of the thermal resistance of resin including its interface according to other embodiments of the invention are shown in FIG. 11 to FIG. 15.

Figure 11:
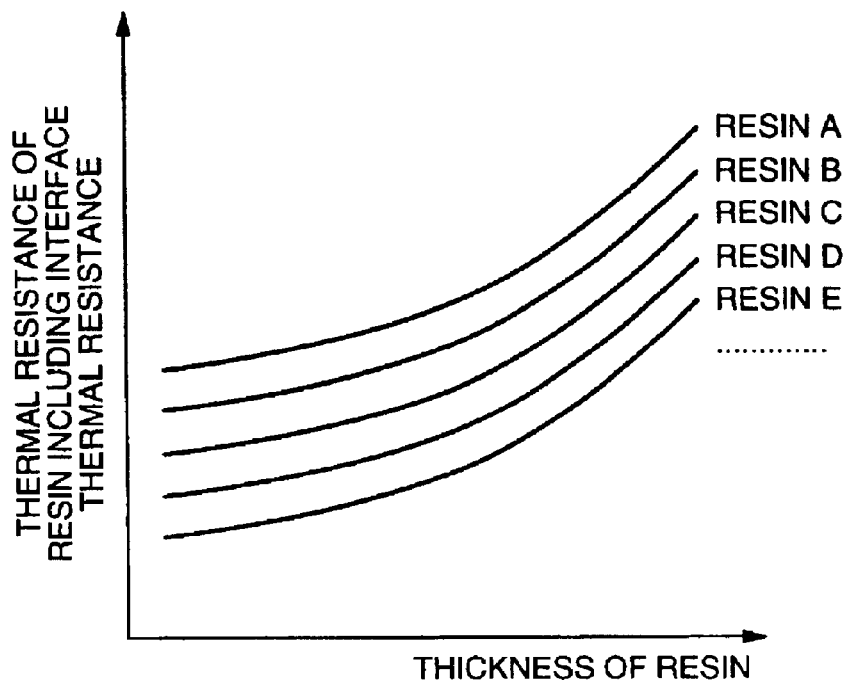
FIG. 11 is a graph for showing a thickness dependence of the thermal resistance of resin.

FIG. 11 is a graph for showing the case of arranging a thickness dependence of the thermal resistance of resin.

In FIG. 11, when the thickness of resin is varied, the composition of the resin completed in a baking process and during curing also varies, and therefore, the thermal resistance caused by conduction of heat in the resin does not change linearly with respect to the thickness of resin. However, the method of conceptual arrangement is shown here. With regard to resins to be compared with reference to, for example, an amount of filler and kind of a filling material, the material of members sandwiching resin therebetween and surface-finishing method therefor are assumed to be common. Thus, samples different in thickness are produced for each of the resins and the thickness dependence is arranged, thereby obtaining the figure shown in FIG. 11.

Figure 12:
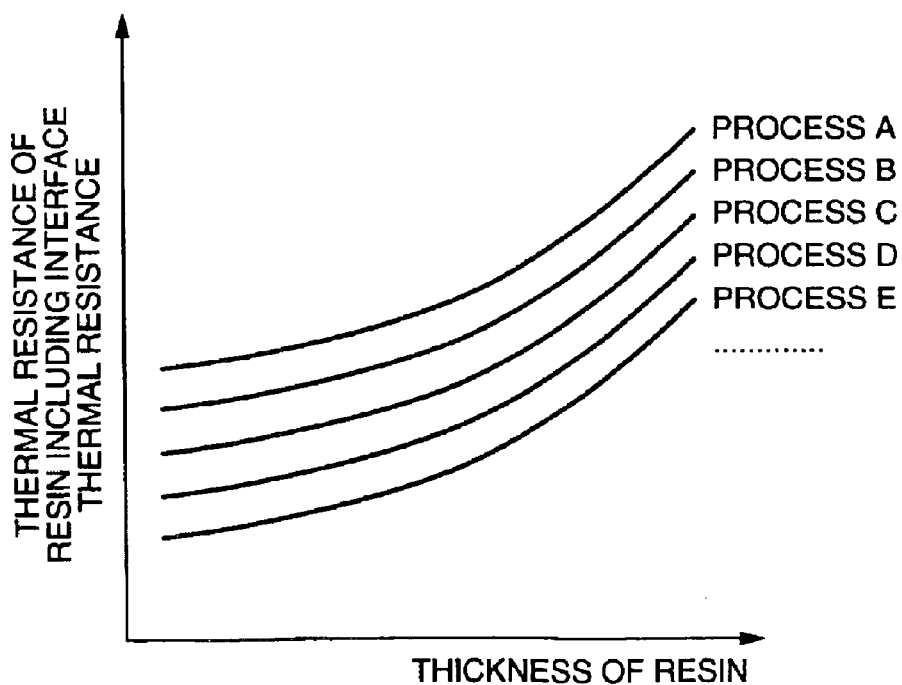
FIG. 12 is a graph for showing the thickness dependence of the thermal resistance of resin.
Figure 13:
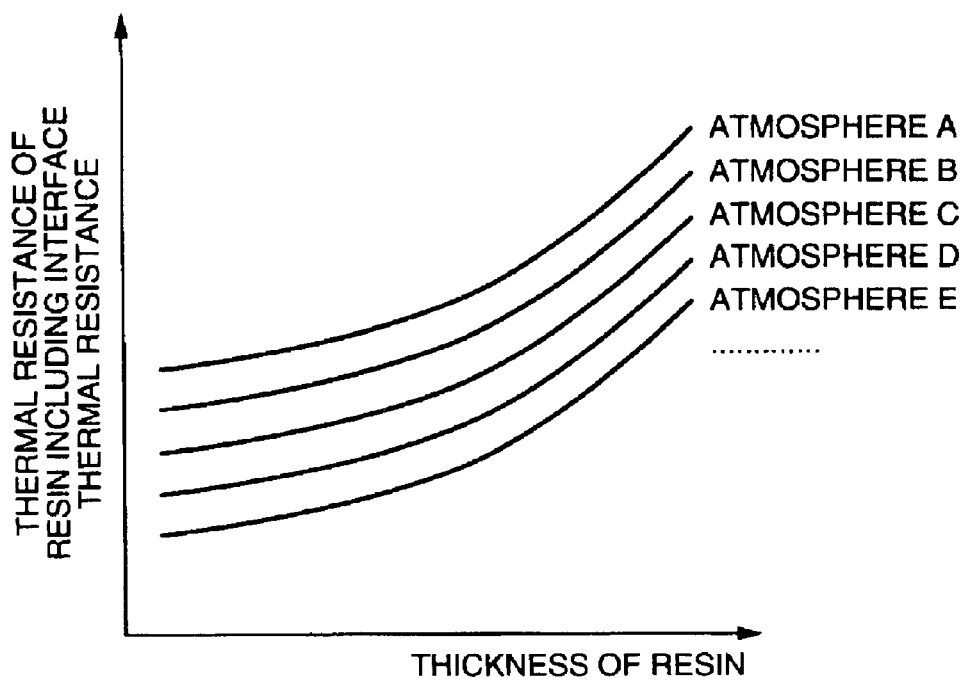
FIG. 13 is a graph for showing the thickness dependence of the thermal resistance of resin.
Figure 14:
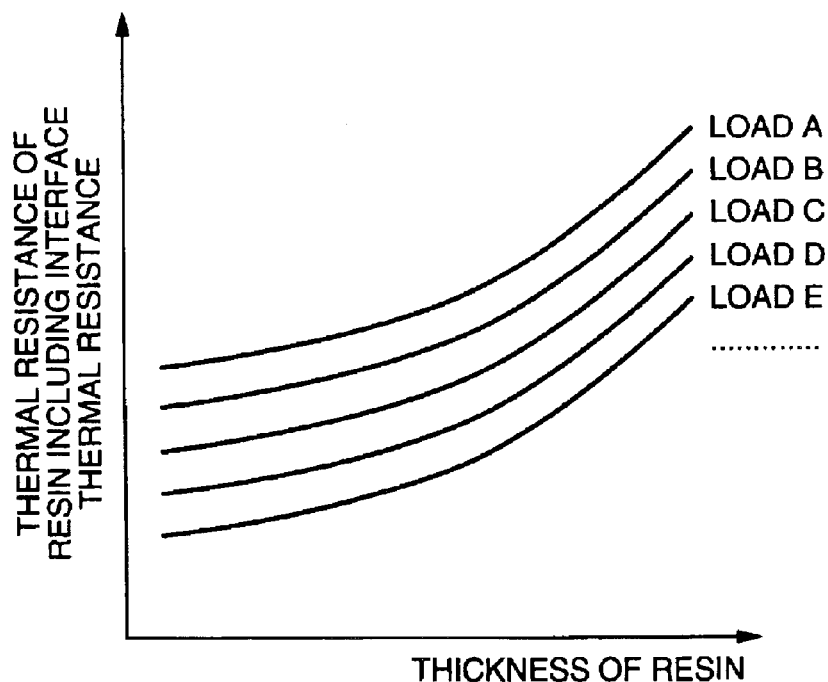
FIG. 14 is a graph for showing the thickness dependence of the thermal resistance of resin.

FIG. 12 is an example of a method of representation for showing the thickness dependence of the same resin produced in different temperature profiles (processes) of the baking process and curing process. Also, FIG. 13 is an example of a method of representation for showing the thickness dependence of the same resin when the atmosphere during measurement, such as temperature and humidity, is varied. FIG. 14 is a diagram for showing the thickness dependence when loads applied to resin are different.

As conceptually shown in FIG. 11 to FIG. 14, in the method of representing and managing the thermal resistance of resin including the information of its interface, there is a method of managing it with reference to the thickness of resin.

Further, instead of such continuous graphs, even if discrete data or even if a form of the discrete data summarized in a table, needless to say, it itself is included in the present invention to measure the thermal resistance of resin including the information of its interface and to treat the results as the thermal resistance of the resin.

Figure 15:
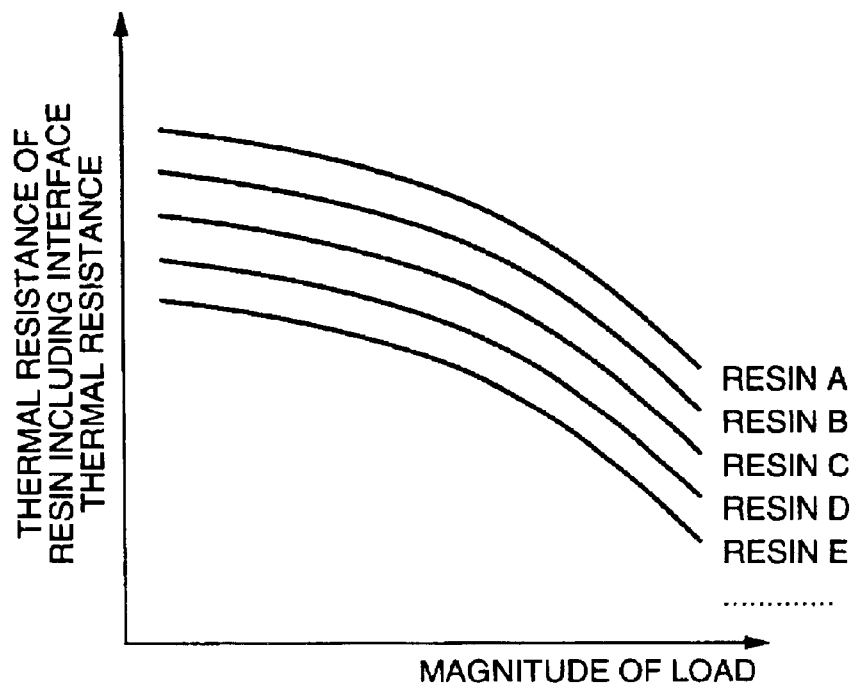
FIG. 15 is a graph for showing a load dependence of the thermal resistance of resin.
Figure 16:
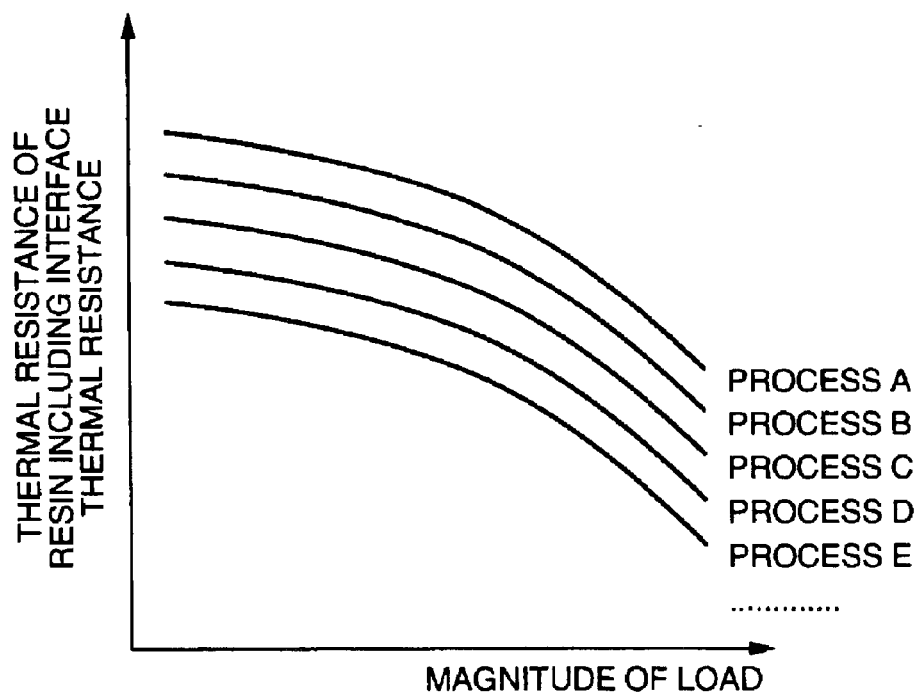
FIG. 16 is a graph for showing the load dependence of the thermal resistance of resin.
Figure 17:
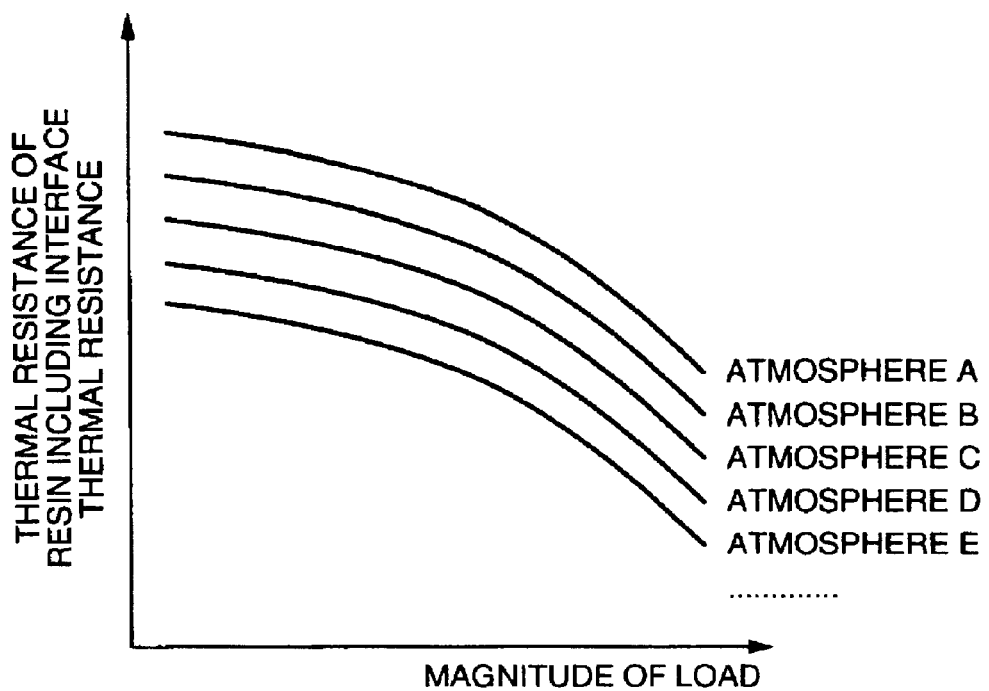
FIG. 17 is a graph for showing the load dependence of the thermal resistance of resin.
Figure 18:
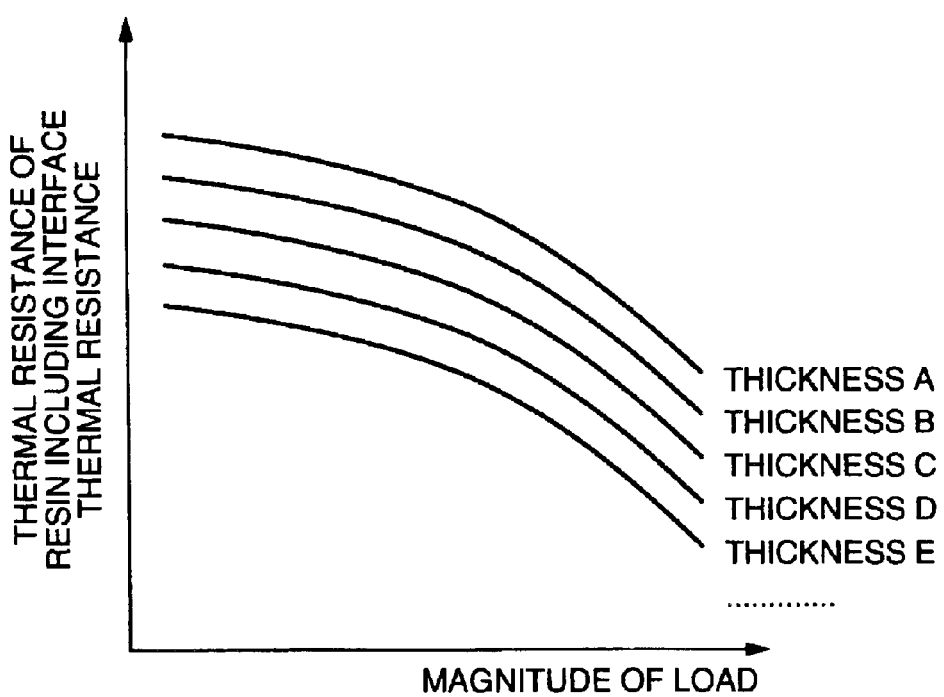
FIG. 18 is a graph for showing the load dependence of the thermal resistance of resin.

FIG. 15 to FIG. 18 are graphs for showing the thermal resistance of resin including the information of its interface with respect to load applied to resin. FIG. 15 shows the load dependence of the thermal resistance with respect to different resins, FIG. 16 shows the load dependence of the thermal resistance in the case of different manufacturing processes, FIG. 17 shows the load dependence of the thermal resistance in the case of different atmospheres, and FIG. 18 shows the load dependence of the thermal resistance in the case of different thicknesses. In this way, in the method of representing and managing the thermal resistance of resin including the information of its interface, there is a method of managing it with reference to the load applied to the resin.

The graphs shown in FIG. 11 to FIG. 14 show the patterns in which the thermal resistance monotonously and nonlinearly increases with respect to thickness, and the graphs shown in FIG. 15 to FIG. 18 show the patterns in which the thermal resistance monotonously and nonlinearly decreases with respect to thickness. These are only conceptual, and there is nothing wrong in that the result of the evaluation of thermal resistance do not show a continuously monotonous change. Also, as parameters for arranging the thickness dependence and load dependence, there are the materials of members sandwiching resin therebetween and the methods of working and finishing, in addition to the kind of resin, process, atmosphere, and thickness or load. Further, when the parameters described above is changed, it is also included in the present invention to represent the dependence on atmosphere, such as atmosphere temperature and to illustrate/arrange the results into data.

Figure 19:
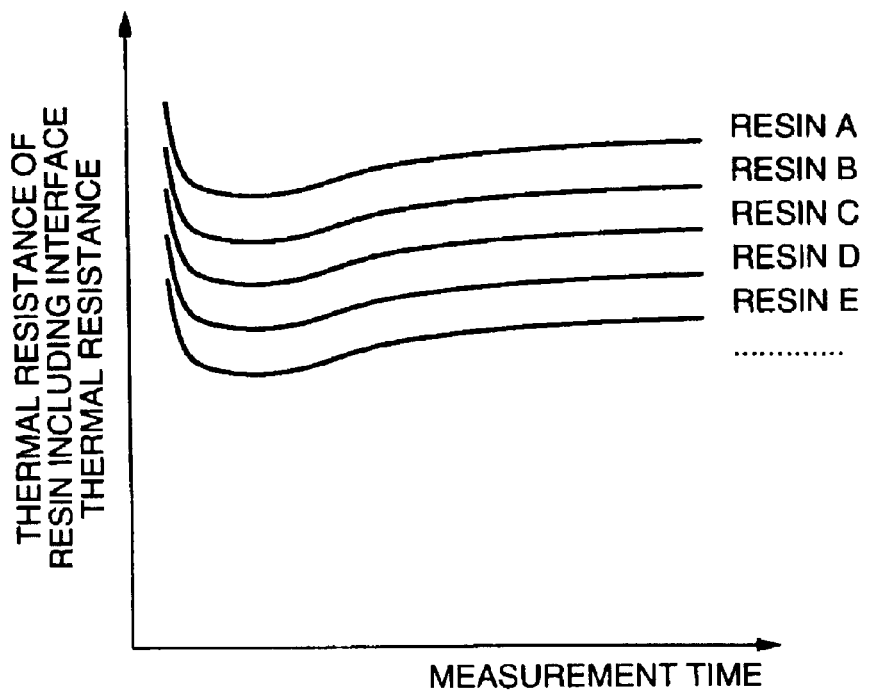
FIG. 19 is a graph for showing a variation with time of the thermal resistance of resin.

FIG. 19 is a graph for representing the variation with time of thermal resistance of resin including the information of its interface according to the present invention. The horizontal axis of the graph is the elapsed time, which includes the case in which a degradation test is carried out for a long time, such as 1000 hours and 10000 hours, and the case in which a test for transient changes is carried out for a shorter time.

FIG. 19 shows the case in which the variation with time of the thermal resistance of resin including the information of its interface is arranged with respect to different resins, and the similar graph can be used to show the cases in which the variation with time is arranged with respect to atmosphere (temperature, humidity, etc.) and load, thickness, and other control parameters.

Further, with regard to control parameters, not only keeping them a constant value but also applying time-based modulation to them are included.

Figure 20:
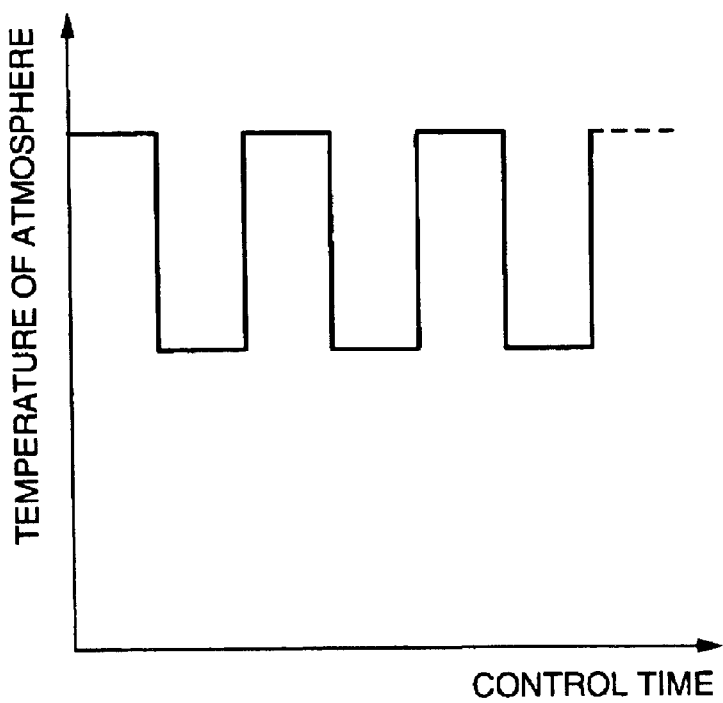
FIG. 20 is a diagram for showing a periodic modulation of an atmosphere temperature applied to resin.

When the atmosphere temperature is periodically changed as shown in FIG. 20, for example, the thermal resistance of resin including the information of its interface at that time can be arranged with respect to the elapsed time from the start of controlling the atmosphere temperature taken on the horizontal axis, with regard to each of control parameters other than temperature, as shown in FIG. 19.

In the present invention, the method of measuring the thermal resistance of resin including the thermal resistance of the interface of the resin has been described. It is also included in the present invention to replace this thermal resistance with an equivalent thermal conductivity and heat transfer coefficient for arranging it.

For example, by replacing Rcond given in the equation (1) with R given in the equation (12) and replacing the thermal conductivity λ with an effective thermal conductivity λeff, the following equation is obtained.

$$\lambda\text{eff}=L/(R\times A)=L/((R\text{int2}+R\text{cond1}+R\text{int3})\times A) \quad (18)$$

Herein, L and A are the length of resin in the direction of passing heat, i.e. the thickness of the resin, and the sectional area of cross-section orthogonal to the direction of passing heat, respectively.

Also, when the effective thermal conductivity between the first member 2 and the second member 3 sandwiching the resin 1 therebetween is assumed to be heff, and the thermal resistance experimentally obtained is assumed to be R, the following relation is given.

$$h\text{eff}=1/(R\times A)=1/((R\text{int2}+R\text{cond1}+R\text{int3})\times A) \quad (19)$$

When these effective thermal conductivity λeff and effective heat transfer coefficient heff are arranged as the material properties, it is included in the present invention that the conversion into the effective thermal conductivity and heat transfer coefficient is performed with reference to thermal resistance measured as the sum of the thermal resistance of interface and the thermal resistance caused by heat conduction, and that such effective thermal conductivity and heat transfer coefficient are managed as data.

Further, although the present invention has been described only with reference to resin, the present invention is applicable to the measurement of effective thermal resistance of all members in which the information of thermal resistance of interfaces is required. Using the same technique for electrically conductive adhesives such as solder, silver paste compounds or the like and for all materials joining solids to solids together such as elastomer, grease or the like, it is possible to measure effective thermal resistance thereof, or to arrange the results as effective thermal conductivity or effective heat transfer coefficient converted therefrom.

Also, the present invention includes measuring material properties including the influence of interfaces of members joining solids to solids, as well as thermal resistance or thermal conductivity or heat transfer coefficient, arranging the results as catalogs and databases, and using them for the purpose of commercial activity.

Also, in the embodiments of the present invention, the cases using the so-called stationary method has been described as methods of measuring thermal resistance. However, there is nothing wrong with using any method, provided that the method permits the measurement of thermal resistance including the information of an interface, which is the object of the present invention.

According to the present invention, it is possible to measure the sum of the thermal resistance caused by conduction of heat through the resin and the thermal resistances of the interfaces between members sandwiching the resin therebetween and the resin as the thermal resistance of the resin. As a result, the thermal resistance of the resin including the information of its interface in the environment during use of actual products can be arranged as databases in a certain stage before mounting the resin on the products, thereby allowing reduction of a trial period in product design and reduction of cost.

Also, according to the present invention, it is possible to define a standard method of measuring thermal resistance for the method of measuring the thermal resistance of resin including the information of its interface. Therefore, it is possible to manage the material properties of the resin in a form made common or standard to both suppliers and users of the resin.

What is claimed is:

1. A method of measuring a thermal resistance of resin, comprising:

sandwiching a resin by a first member and a second member to form a laminated structure;

applying a load through a third member and a fourth member to the laminated structure, causing heat to flow consecutively through said third member, said first member, said resin, said second member, and said fourth member, or consecutively through said fourth member, said second member, said resin, said first member, and said third member;

measuring a thermal resistance including a thermal resistance of an interface between said third member and said first member, a thermal resistance caused by conduction of heat through said first member, a thermal resistance of an interface between said first member and said resin, a thermal resistance caused by conduction of heat through said resin, a thermal resistance of an interface between said resin and said second member, a thermal resistance caused by conduction of heat through said second member, and a thermal resistance of an interface between said second member and said fourth member while controlling the load so as to become a desired value on the basis of a measured value of the load applied to the laminated structure; and subtracting the thermal resistance of the interface between said third member and said first member, the thermal resistance caused by conduction of heat through said first member, the thermal resistance caused by conduction of heat through said second member, and the thermal resistance of the interface between said second member and said fourth member, which resistances have been obtained beforehand from thermal resistance measured, whereby the thermal resistance of the interface between said resin and said first member, the thermal resistance caused by conduction of heat through said resin, and the thermal resistance of the interface between said resin and said second member are determined as a thermal resistance including interface information of the resin layer.

2. A method of measuring a thermal resistance of resin according to claim 1, comprising a step of measuring an initial value and variation with time of the thermal resistance of said resin.

3. A method of measuring a thermal resistance of resin according to claim 1, wherein said controlling the load is more specifically dynamically controlling the load so as to become a desired value on the basis of a dynamically measured value of the load applied to the laminated structure.

4. A method of measuring a thermal resistance of resin according to claim 1,
wherein variation of the load with respect to elapse of time during measurement is restrained on the basis of a measured value of the load applied to the laminated structure.

5. A method of measuring a thermal resistance of resin according to claim 4, wherein said restraining variation is more specifically dynamically restraining variation of the load with respect to elapse of time during measurement on the basis of a dynamically measured value of the load applied to the laminated structure.

6. A method of measuring a thermal resistance of resin according to claim 1,
wherein the load to restrain variation of height of the laminated structure with respect to elapse of time during measurement is controlled on the basis of a measured value of the load applied to the laminated structure.

7. A method of measuring a thermal resistance of resin according to claim 6, wherein said controlling is more specifically dynamically controlling the load to restrain variation of height of the laminated structure with respect to elapse of time during measurement on the basis of a dynamically measured value of the load applied to the laminated structure.

8. A method of measuring a thermal resistance of resin according to claim 1, comprising:
arranging as a database the results obtained by measuring the variation with time of said thermal resistance of resin including interface information of said resin layer; and
applying said database to a design of thermal structure of a device on which said resin is mounted.

9. A method of measuring a thermal resistance of resin according to claim 8, comprising measuring said thermal resistance of resin including interface information of said resin layer when factors having an influence on said thermal resistance of resin are kept constant.

10. A method of measuring a thermal resistance of resin according to claim 8, comprising measuring said thermal resistance of resin including interface information of said resin layer when factors having an influence on said thermal resistance of resin are varied in accordance with a fixed condition.

11. An apparatus for measuring a thermal resistance of resin, comprising:
a first member and a second member for sandwiching a resin therebetween to form a laminated structure;
a third member and a fourth member for applying load from both sides of a laminated structure;
means for causing heat to flow consecutively through said third member, said first member, said resin, said second member, and said fourth member, or consecutively through said fourth member, said second member, said resin, said first member, and said third member;
means for measuring a thermal resistance including a thermal resistance of an interface between said third member and said first member, a thermal resistance caused by conduction of heat through said first member, a thermal resistance of an interface between said first member and said resin, a thermal resistance caused by conduction of heat through said resin, a thermal resistance of an interface between said resin and said second member, a thermal resistance caused by conduction of heat through said second member, and a thermal resistance of an interface between said second member and said forth member while controlling the load so as to become a desired value on the basis of a measured value of the load applied to the laminated structure; and
means for subtracting the thermal resistance of the interface between said third member and said first member, the thermal resistance caused by conduction of heat through said first member, the thermal resistance caused by conduction of heat through said second member, and the thermal resistance of the interface between said second member and said fourth member, which resistances have been determined beforehand from the thermal resistance measured,
whereby the thermal resistance of the interface between said resin and said first member, the thermal resistance caused by conduction of heat through said resin, and the thermal resistance of the interface between said resin and said second member is determined as a thermal resistance including interface information of the resin layer.

12. An apparatus for measuring a thermal resistance of resin according to claim 11, wherein said controlling the load is more specifically dynamically controlling the load so as to become a desired value on the basis of a dynamically measured value of the load applied to the laminated structure.

* * * * *